US012799496B2

(12) United States Patent
Harriman et al.

(10) Patent No.: US 12,799,496 B2
(45) Date of Patent: Nov. 17, 2026

(54) TRANSGENIC PLANT, METHODS AND COMPOSITIONS FOR PRODUCING THE SAME

(71) Applicant: Medgro Bio, Inc., Buffalo, NY (US)

(72) Inventors: Bob Harriman, Delware, OH (US); Paul Rushton, Amherst, NY (US); Sujon Sarowar, East Amherst, NY (US)

(73) Assignee: Medgro Bio, Inc., Buffalo, NY (US)

( * ) Notice: Subject to any disclaimer, the term of this patent is extended or adjusted under 35 U.S.C. 154(b) by 0 days.

(21) Appl. No.: 19/061,325

(22) Filed: Feb. 24, 2025

(65) Prior Publication Data

US 2026/0250703 A1 Aug. 27, 2026

(51) Int. Cl.
*C12N 15/82* (2006.01)
*C12N 9/00* (2006.01)
*C12N 9/02* (2006.01)

(52) U.S. Cl.
CPC ....... *C12N 15/8261* (2013.01); *C12N 9/0071* (2013.01)

(58) Field of Classification Search
CPC .......................... C12N 15/8261; C12N 9/0071
See application file for complete search history.

(56) References Cited

U.S. PATENT DOCUMENTS

| | | | |
|---|---|---|---|
| 4,959,317 | A | 9/1990 | Sauer |
| 5,352,605 | A | 10/1994 | Fraley et al. |
| 5,527,695 | A | 6/1996 | Hodges et al. |
| 5,550,318 | A | 8/1996 | Adams et al. |
| 5,633,435 | A | 5/1997 | Barry et al. |
| 5,780,708 | A | 7/1998 | Lundquist et al. |
| 6,118,047 | A | 9/2000 | Anderson et al. |
| 6,194,636 | B1 | 2/2001 | McElroy et al. |
| 6,232,526 | B1 | 5/2001 | McElroy et al. |
| 11,046,969 | B2 | 6/2021 | Jia et al. |
| 11,512,322 | B2 | 11/2022 | Jia et al. |
| 11,891,610 | B2 * | 2/2024 | Jia .................. C12Y 114/11033 |
| 12,145,967 | B2 | 11/2024 | Alves-Junior et al. |
| 2018/0340182 | A1 | 11/2018 | Jia et al. |
| 2023/0210073 | A1 | 7/2023 | Di et al. |
| 2024/0318193 | A1 | 9/2024 | Jia et al. |

FOREIGN PATENT DOCUMENTS

| | | | |
|---|---|---|---|
| CN | 104513831 | A | 4/2015 |
| WO | 9966785 | A1 | 12/1999 |
| WO | 2024211438 | A2 | 10/2024 |

OTHER PUBLICATIONS

Guo et al. (Published Year: 2004, Journal: Proceedings of the National Academy of Sciences, vol. 101(25), pp. 9205-9210). (Year: 2004).*

Shen et al. (Published: 2023, Journal: Genome Biology 24:43 p. 1-24 https://doi.org/10.1186/s13059-023-02872-6). (Year: 2023).*

Yu et al. (Published 2021, Journal: Nature Biotechnology 39: 1581-1588 | www.nature.com/naturebiotechnology). (Year: 2021).*

Ahmed et al. (Published: 2019, Journal: Sarhad Journal of Agriculture 35(2):500-512). (Year: 2019).*

Yue et al. (Published: 2019, Journal: Plant Biotechnology Journal 17, pp. 1194-1208). (Year: 2019).*

JGI BLAST search results for *Ostreococcus* sp. RCC809, (accessed at https://mycocosm.jgi.doe.gov/, database published on Jul. 2009). (Year: 2009).*

Delwiche et al. (Published: 2011, Journal: Current Biology 21(11): R417-R422, see p. 6, summary). (Year: 2011).*

Chinnusamy, V. et al. RNA-directed DNA methylation and demethylation in plants. Sci China C Life Sci. Apr. 2009;52(4):331-43.

Das, S. et al. (2023) Role of biotechnology in creating sustainable agriculture. PLOS Sustain Transform 2(7): e0000069.

Duan, H. et al., ALKBH10B is an RNA N.SUP.6.-Methyladenosine Demethylase Affecting *Arabidopsis* Floral Transition, The Plant Cell, 29:2995-3011 (2017).

Huong et al., "Functional Characterization of a Putative RNA Demethylase ALKBH6 in *Arabidopsis* Growth and Abiotic Stress Responses," International Journal of Molecular Sciences, Sep. 13, 2020, 14 pages.

Jia, G. et al., Reversible RNA adenosine methylation in biological regulation, Trends Genet., 29(2):108-15 (2013).

Li, Y. et al. Active DNA demethylation: mechanism and role in plant development. Plant Cell Rep. Jan. 2018;37(1):77-85.

Luo et al., "Unique features of the m6A methylome in *Arabidopsis thaliana*," nature communication, Nov. 28, 2014, 8 pages.

Roundtree, I. et al. Dynamic RNA Modifications in Gene Expression Regulation, Cell, vol. 169, Issue 7, (2017), pp. 1187-1200.

Selvaraj, M. et al. Overexpression of an *Arabidopsis thaliana* galactinol synthase gene improves drought tolerance in transgenic rice and increased grain yield in the field, Plant Biotechnology Journal (2017) 15, pp. 1465-1477.

Shinde, H. et al. (2023) RNA methylation in plants: An overview. Front. Plant Sci. 14:1132959.

Tang, J. et al. (2023). Detection, regulation, and functions of RNAN6-methyladenosinemodification in plants. Plant Comm. 4, 100546.

Wang et al., "Coordinated regulation of vegetative and reproductive branching in rice," CrossMark, vol. 112, No. 50, Dec. 15, 2015, 6 pages.

(Continued)

*Primary Examiner* — David H Kruse
*Assistant Examiner* — Santosh Sharma
(74) *Attorney, Agent, or Firm* — Jeff B. Vockrodt; CM Law

(57) ABSTRACT

The invention relates to biotechnology and provides novel engineered protein for conferring enhanced growth. The invention also provides transgenic plants, seeds, cells and plant parts containing recombinant DNA molecules, as well as methods of using the same.

16 Claims, 5 Drawing Sheets

Specification includes a Sequence Listing.

(56) References Cited

OTHER PUBLICATIONS

Wei, L. et al., The m.SUP.6.A Reader ECT2 Controls Trichome Morphology by Affecting mRNA Stability in *Arabidopsis*, The Plant Cell, 30:968-985 (2018). doi: 10.1111/pbi.12731.

Yu, Q. et al. RNA demethylation increases the yield and biomass of rice and potato plants in field trials. Nat Biotechnol 39, 1581-1588 (2021).

Zhang, H., and Zhu, J.K. (2022). Active DNA demethylation in plants: 20 years of discovery and beyond. J. Integr. Plant Biol. 64: 2217-2239.

Gils, "Transformation vector pICH14313," National Center for Biotechnology Information, Mar. 18, 2008, 4 pages.

Search Report received in International Application No. PCT/US2026/016433 dated Jul. 20, 2026, 6 pages.

Written Opinion received in International Application No. PCT/US2026/016433 dated Jul. 20, 2026, 13 pages.

* cited by examiner

Control Line #1 Line #2

TRANSGENIC PLANT, METHODS AND COMPOSITIONS FOR PRODUCING THE SAME

BACKGROUND OF THE INVENTION

(i) Field of the Invention

This disclosure relates to the compositions and methods for improving plant development and stress tolerance in plants.

(ii) Sequence Listing

The Sequence Listing in an ASCII text file, named 100020_00001_Sequence_Listing.txt of 9.56 KB, created on Apr. 28, 2025, and submitted to the United States Patent and Trademark Office via EFS-Web, is incorporated herein by reference.

(iii) Description of Related Art

To nourish an increasing population both physically and mentally, developing plant varieties that are more productive and tolerant to stress is a critical goal of plant scientists. Plant biotechnology has played a significant role in increasing crop production (Das et al., Selvaraj et al., Various transgenes have been used to increase crop production (U.S. Pat. Nos. 12,145,967 and 11,046,969).

Methylation and Demethylation of both DNA and RNA play vital roles in gene expression (Li et al, Zhang et al, Roundtree et al). DNA demethylation has been shown to affect such plant development as stomatal development, pollen germination, fruit ripening, branching and endosperm as well as embryo development (Li et al., Wei et al., Wang et al., Duan et al.). DNA methylation and demethylation which can be directed by RNA as occurs with small interfering RNAs direct the cytosine methylation of DNA sequences complementary to the small interfering RNA (Chinnusamy et al). Of particular interest, is work by Yu et al. that showed RNA demethylation increases the yield and biomass of rice and potato. Several patents have been granted for increasing yield by expressing $m^6A$ demethylase FTO genes from humans, pig, cattle and green algae (U.S. Pat. Nos. 11,046,969; 11,512,322; 11,891,610 and U.S. Pat. App. Pub. No. 2018-0340182).

There remains a need to identify new variants capable of expressing $m^6A$ demethylase FTO genes to provide improved speed of plant development and/or stress tolerance in one or more plant species.

SUMMARY OF THE INVENTION

The present invention relates to the demethylation of RNA. Cellular RNA molecules, including tRNAs, rRNAs and mRNAs, have been shown to be involved with 100 types of chemical modifications (Roundtree et al.). The most common mRNA modification is N6-methyladenosine ($m^6A$) (Shinde et al.). These modifications have been associated with plant development such as root growth, organ development, fruit ripening and callus induction (Shinde et al., Tang et al., Yu et al.).

The present invention provides novel engineered protein for conferring enhanced growth. More specifically, the invention relates to recombinant DNA molecules encoding enzymes that confer demethylase activity of RNA.

More particularly, in a first aspect provided herein are polynucleotides encoding a polypeptide comprising an amino acid sequence that is at least 95% identical to an amino acid or the full length sequence comprising SEQ ID: 1.

In a second aspect, the invention provides recombinant DNA constructs comprising a regulatory element operably linked to a polynucleotide encoding a polypeptide comprising an amino acid sequence that is at least 95% identical to an amino acid sequence or the full length sequence comprising SEQ ID: 1. In certain embodiments the regulatory element is a heterologous promoter, such as for example, 35S strong constitutive promoter or GOS2 moderately constitutive promoter.

In another aspect, provided are plant cells, plants, and seeds comprising the polynucleotide encoding a polypeptide or the recombinant DNA construct comprising a regulatory element operably linked to the polynucleotide encoding a polypeptide at least 95% identical to the amino acid of SEQ ID: 1. In certain embodiments, the regulatory element is a heterologous promoter. In certain embodiments, the plant and/or seed is from a dicot plant. In certain embodiments, the dicot plant is tobacco.

In yet another aspect, provided are methods for increasing yield in a plant by expressing in a regenerable plant cell a recombinant DNA construct comprising a regulatory element operably linked to a polynucleotide encoding a polypeptide comprising an amino acid sequence that is at least 95% identical to an amino acid sequence of SEQ ID: 1; and generating the plant, wherein the plant comprises in its genome the recombinant DNA construct. In certain embodiments, the regulatory element is a heterologous promoter. In certain embodiments, the plant is a dicot plant. In certain embodiments, the dicot plant is tobacco. In certain embodiments, the increase yield is more biomass.

In another aspect, the invention provides methods for increasing yield in a plant by introducing in a regenerable plant cell a targeted genetic modification at a genomic locus that encodes a polypeptide comprising an amino acid sequence that is at least 90%, 91%, 92%, 93%, 94%, 95%, 96%, 97%, 98%, 99% identical to an amino acid sequence or the full length sequence comprising SEQ ID: 1; and generating the plant, wherein the level and/or activity of the encoded polypeptide is increased in the plant. In certain embodiments, the genetic modification is introduced using an expression cassette utilizing 35S promoter driving SEQ ID 2. In certain embodiments, the plant cell is from a dicot plant. In certain embodiments, the dicot plant is tobacco. In certain embodiments, the increased yield is increased biomass.

In one embodiment, said nucleic acid molecule encoding the $m^6A$ demethylase has at least 90%, preferably at least 95%, more preferably at least 99%, most preferably 100% identity to SEQ ID: 2.

The transgenic plant of the present invention exhibits an increased biomass, an increased yield or the combination thereof when compared with a control plant which does not comprise the nucleic acid molecule encoding the $m^6A$ demethylase.

In one embodiment, the plant of the present invention is wheat, rice, corn, soybean, canola, tobacco, potato, alfalfa, canola, cotton, sunflower, *cannabis*, turfgrass or ornamentals. The present invention is also directed to a tissue, an organ, a pollen, a seed, a grain, a fruit and a progeny plant of the aforesaid transgenic plant.

BRIEF DESCRIPTION OF THE DRAWINGS AND SEQUENCE LISTING

Figure 1:
FIG. 1 shows the enhanced growth and superior development of three tobacco plants expressing demethylase gene from Ostreococcus RCC809 versus control tobacco plants not expressing the demethylase gene.
Figure 2:
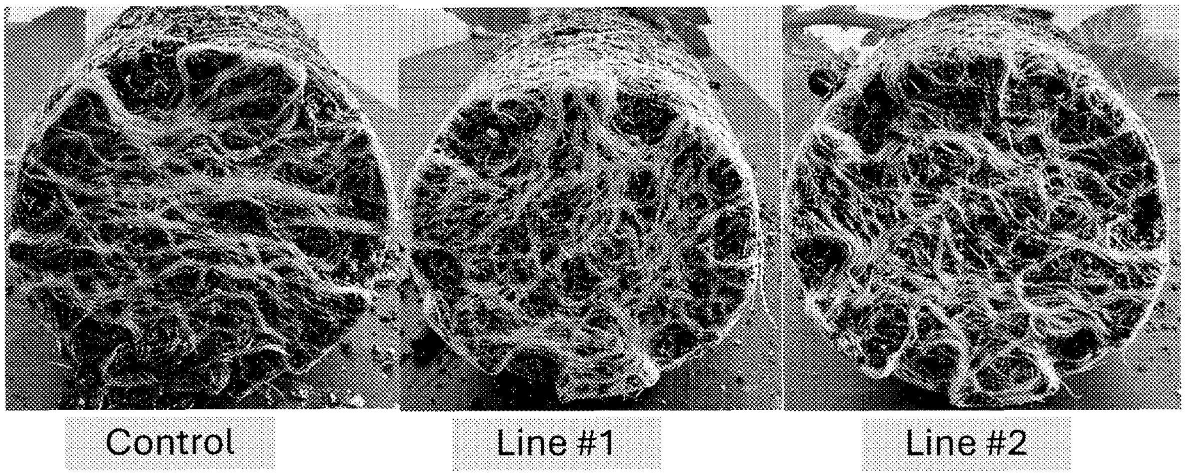
FIG. 2 shows enhanced root development of two independent transgenic tobacco lines expressing demethylase gene from Ostreococcus RCC809 versus control tobacco plants not expressing the demethylase gene.
Figure 3:
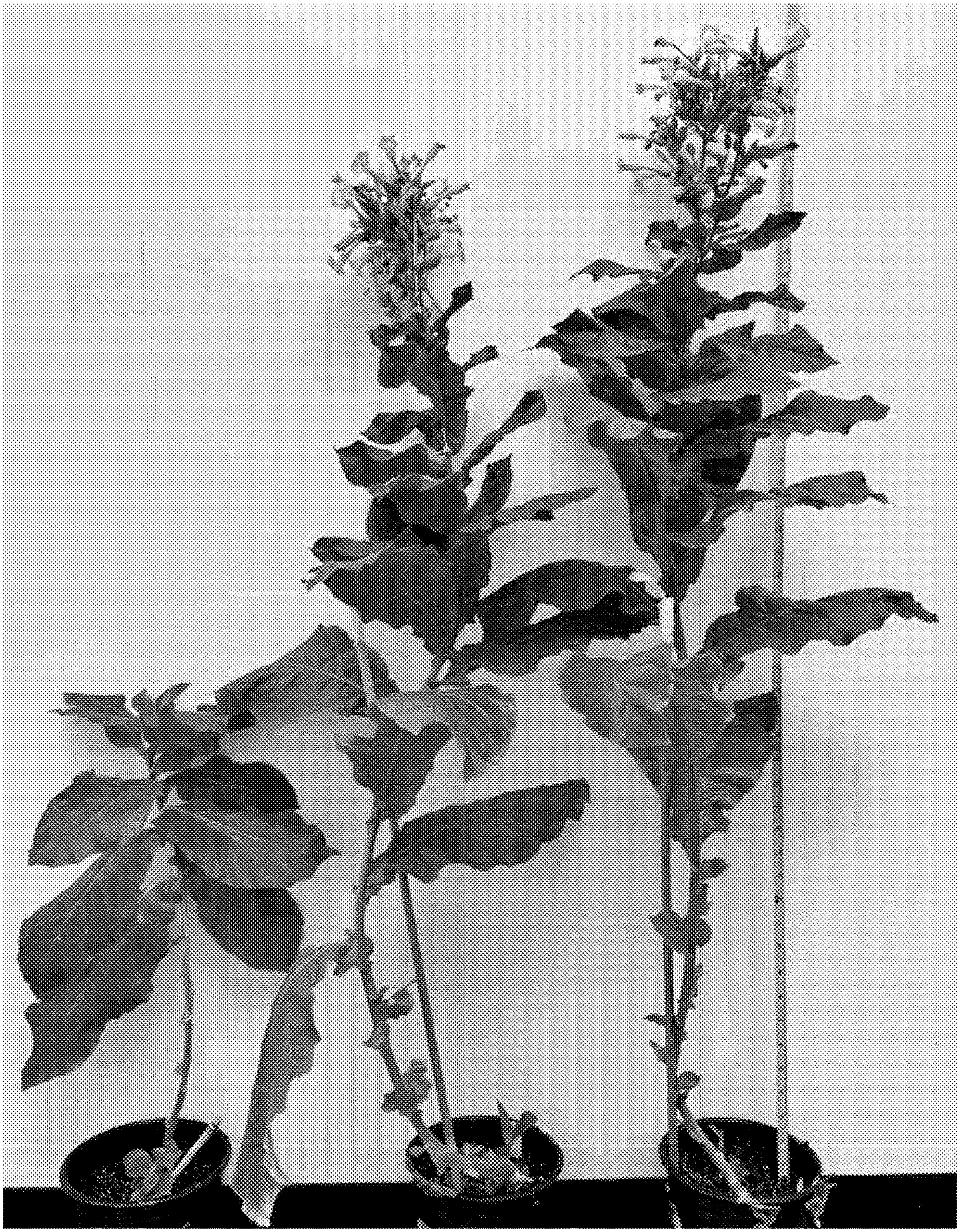
FIG. 3 shows faster plant development and earlier flowering of two independent transgenic tobacco lines expressing demethylase gene from Ostreococcus RCC809 versus control tobacco plants not expressing the demethylase gene.
Figure 4:
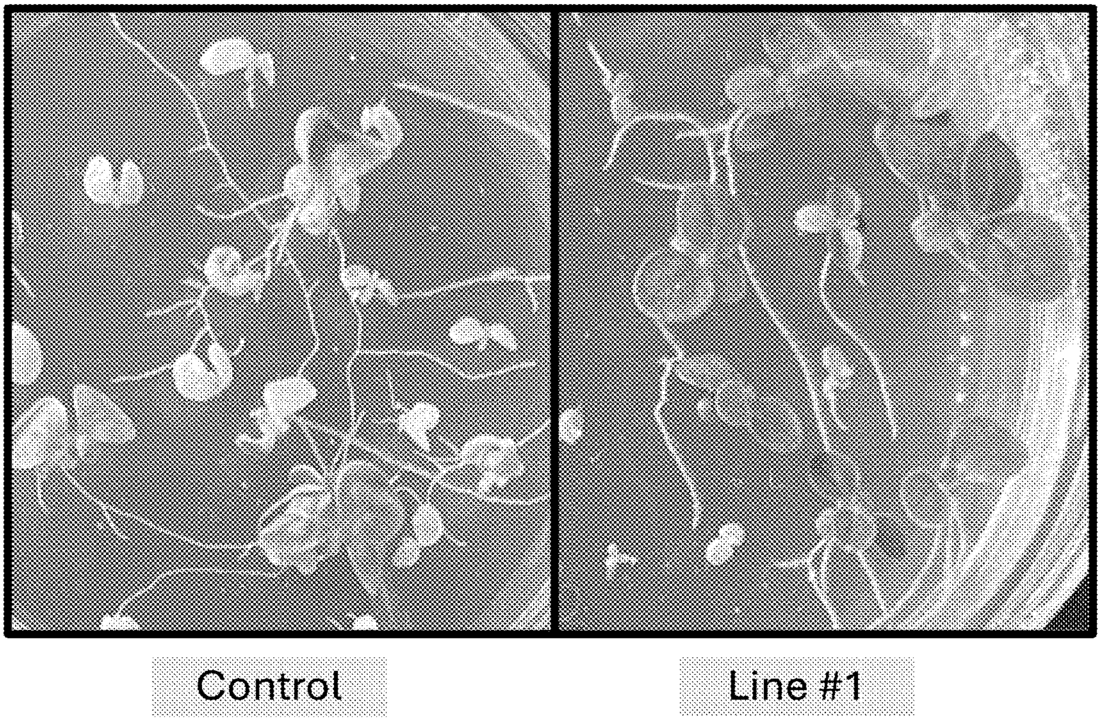
FIG. 4 shows enhanced salt stress tolerance of tobacco seedlings expressing demethylase gene from Ostreococcus RCC809 grown on 200 mM sodium chloride versus control tobacco seedlings not expressing the demethylase gene.
Figure 5:
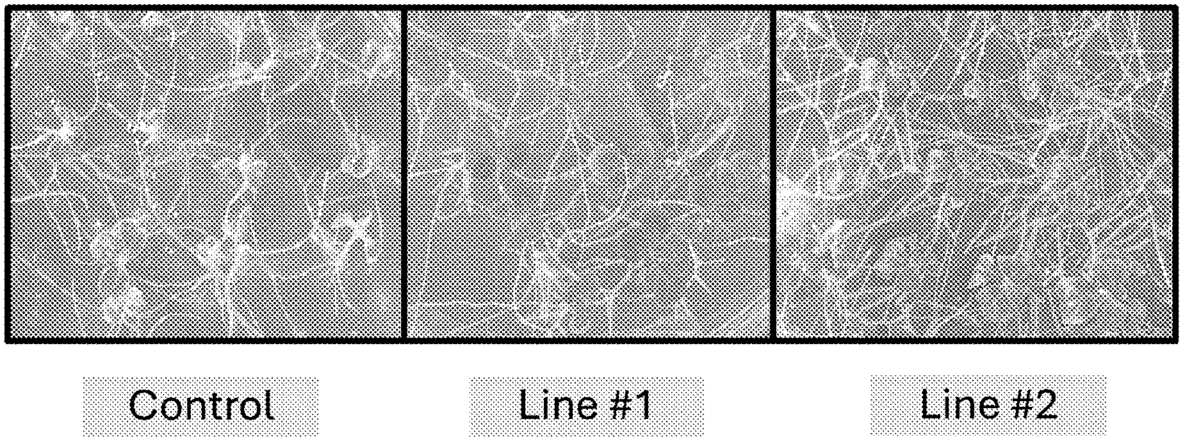
FIG. 5 shows enhanced salt stress tolerance of tobacco seedlings expressing demethylase gene from Ostreococcus RCC809 grown on 300 mM mannitol versus control tobacco seedlings not expressing the demethylase gene.
Figure 6:
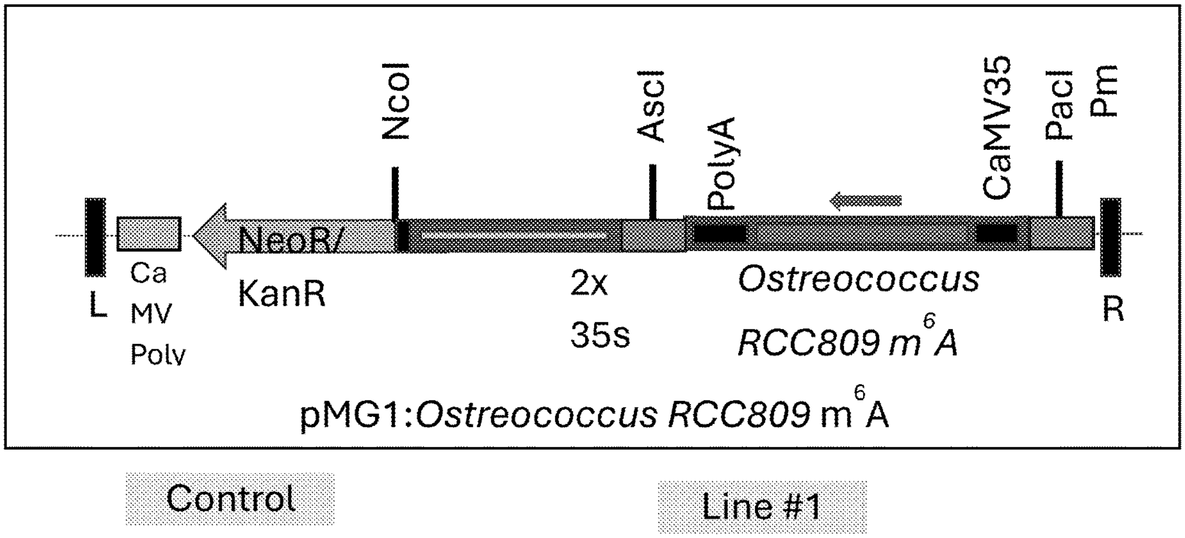
FIG. 6 shows expression cassette.

SEQ ID NO: 1 Ostreococcus RCC809 demethylase amino acid sequence.

SEQ ID NO: 2 Ostreococcus RCC809 demethylase nucleotide sequence.

SEQ ID NO: 3 Ostreococcus RCC809 FTO gene in pFAT1.

The disclosure can be more fully understood from the following detailed description and the accompanying drawings and Sequence Listing, which form a part of this application.

The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

DETAILED DESCRIPTION

I. Composition

A. Polynucleotides and Polypeptides

The present disclosure provides polynucleotides encoding polypeptides. Accordingly, as used herein “polypeptide,” “protein,” or the like, refers to a protein represented by a SEQ ID NOs. 1 & 2. One aspect of the disclosure provides a polynucleotide encoding a polypeptide comprising an amino acid sequence that is at least 90-99% % identical to the amino acid sequence of SEQ ID NO: 1.

$m^6A$ demethylase and the nucleic acids encoding said demethylase may be used to produce the transgenic plant of the present invention. The $m^6A$ demethylase used by the present invention was identified in Ostreococcus sp. RCC809., which differs from the $m^6A$ demethylase disclosed in U.S. Pat. Nos. 11,046,969; 11,512,322; 11,891,610 and U.S. Pat. App. Pub. No. 2018-0340182. The $m^6A$ demethylase of SEQ ID NO: 1 has only 30%, 29%, 30% and 70% protein homology to the human (’969 patent, SEQ ID NO: 1), pig (’969 patent, SEQ ID NO: 2), cattle (’969 patent, SEQ ID NO: 3) and green alga (’969 patent, SEQ ID NO: 4). The present inventors have observed qualitative improvements in 1) speed of plant development and 2) stress tolerance (osmotic) for the $m^6A$ demethylase of the present invention.

As used herein “homolog” means a protein that perform the same biological function. Homologs are expressed by homologous genes. Homologous genes include naturally occurring alleles and artificially created variants. Homologs are proteins that when aligned have at least 90%, preferable at least 95% identity over the full length of a protein identified as increasing the yield and/or biomass or stress tolerance of plants when expressed in plant cells.

Homologs are identified by comparison of amino acid sequence, e.g. manually or by use of a computer-based tool using known homology-based search algorithms such as those commonly known and referred to as BLAST, FASTA, and Smith-Waterman. A further aspect of the homologs encoded by DNA useful in the transgenic plants of the invention are those proteins that differ from a disclosed protein as the result of deletion or insertion of one or more amino acids in a native sequence.

As used herein, “percent identity” means the extent to which two optimally aligned DNA or protein segments are invariant throughout a window of alignment of components, for example nucleotide sequence or amino acid sequence. An “identity fraction” for aligned segments of a test sequence and a reference sequence is the number of identical components that are shared by sequences of the two aligned segments divided by the total number of sequence components in the reference segment over a window of alignment which is the smaller of the full test sequence or the full reference sequence. “Percent identity” (“% identity”) is the identity fraction times 100.

The $m^6A$ demethylase used in the present invention may be SEQ ID NO: 1 of the homolog thereof. Said homolog has at least 90%, 91%, 92%, 93%, 94%, 95%, 96%, 97%, 98%, or 99% sequence identity to any one of SEQ ID: 1.

The nucleic acid encoding the $m^6A$ demethylase used in the present invention may be any one of SEQ ID 2 or the homologous gene thereof. Said homologous gene has at least 90%, 91%, 92%, 93%, 94%, 95%, 96%, 97%, 98%, or 99% sequence identity to any one of SEQ ID NO: 2.

The nucleic acid encoding the $m^6A$ demethylase defined herein may not be a full-length nucleic acid. A part of the nucleic acid encoding the $m^6A$ demethylase defined herein may be prepared by making one or more deletions from the full-length nucleic acid.

All or a portion of the nucleic acids of the present invention may be synthesized using codons preferred by a selected host. Species-preferred codons may be determined, for example, from the codons used most frequently in the proteins expressed in a particular host species. Therefore, the nucleic acids of the present invention include those obtained by making codon-optimization to natural $m^6A$ demethylase for the expression in plants. Other modifications of the nucleotide sequences may result in mutants having slightly altered activity.

The present invention is directed to a transgenic plant in which a gene encoding the aforesaid $m^6A$ demethylase or a homolog thereof is introduced, or a progeny plant thereof. The present invention is also directed to a cell, a tissue, an organ, a pollen, a seed, a grain, a tuber, a stolon, a rhizome or a fruit of said plant.

“Introduced” in the context of inserting a nucleic acid fragment (e.g., a recombinant DNA construct) into a cell, means “transfection” or “transformation” or “transduction” and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, stolons, rhizomes, tubers, fruits, gametophytes, sporophytes, pollen, and microspores. "Progeny" comprises any subsequent generation of a plant.

According to the use, the plants of the present invention may be food crops, economic crops, vegetable crops, fruits, flowers, grasses, trees, industrial raw material crops, feed crops or medicine crops. Specifically, said food crops include rice, maize, soybean, beans, yams, potato, barley, broad bean, wheat, barley, millet, rye, oat, sorghum, etc.; Said economic crops include oil tea, rape, rapeseed, flax, false flax (*Camelina sativa*), peanut, oil flax (*Linum usitatissimum*), marijuana (*Cannabis sativa*), sunflower, tobacco, cotton, beet, sugarcane, etc.; said vegetable crops include radish, Chinese cabbage, tomato, cucumber, hot pepper, carrot, etc.; said fruits include pear, apple, walnut, cherry, strawberry, blueberry, raspberry, blackberry, jujube or peach; said flowers include flowers for view, for example, orchid, *Chrysanthemum*, carnation, rose, petunia, geranium, vinca, impatiens, green plants, etc., grasses for example creeping bentgrass, tall fescue, ryegrass, St. Augustinegrass, zoysia, bermudagrass and trees include *Populus, Hevea brasiliensis, Taxus chinensis*, and those for urban greening or those living in deserts and harsh conditions such as drought; said industrial raw material crops include Russian dandelion, guayule, *Jatropha curcas*, etc., said feed crops include the foodstuff for livestock, such as alfalfa etc.; said drug crops include *Ginseng, Angelica* and *Ganoderma*, etc.

"Transgenic plant" includes reference to a plant which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

The DNA construct of the present invention comprises a nucleic acid molecule encoding the $m^6A$ demethylase protein described herein. The construct may comprise the nucleic acid molecule encoding the $m^6A$ demethylase protein described herein optionally operably linked to a promoter sequence which functions in a host cell. Other construct components may include additional regulatory elements, such as 5' leaders and introns for enhancing transcription, 3' untranslated regions (such as polyadenylation signals and sites), DNA for transit, signal peptides, or one or more selective maker genes.

As used herein, "promoter" means regulatory DNA for initializing transcription. A plant promoter is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions. Promoters useful in the present invention are not specifically limited. Those skilled in the art may select suitable promoters according to their knowledge.

As used herein "operably linked" means the association of two or more DNA fragments in a DNA construct so that the function of one, e.g. protein-encoding DNA, is controlled by the other, e.g. a promoter.

The DNA construct generally includes a selective maker gene. Selective marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (npt11), hygromycin B (aph IV) and gentamycin (aac3 and aacC4) or resistance to herbicides such as glufosinate (bar or pat) and glyphosate (aroA or EPSPS). Examples of such selective markers are illustrated in U.S. Pat. Nos. 5,550,318; 5,633,435; 5,780,708 and 6,118,047, all of which are incorporated herein by reference. Selective markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

The introduction of the recombinant DNA construct into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. For *Agrobacterium tumefaciens* based plant transformation system, additional elements present on transformation constructs will include T-DNA left and right border sequences to facilitate incorporation of the recombinant polynucleotide into the plant genome.

In general, it is useful to introduce recombinant DNA randomly, i.e. at a non-specific location, in the genome of a target plant line. In special cases it may be useful to target recombinant DNA insertion to achieve site-specific integration, for example to replace an existing gene in the genome, to use an existing promoter in the plant genome, or to insert a recombinant polynucleotide at a predetermined site known to be active for gene expression. Several site-specific recombination systems exist which are known to function in plants include cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, for example various media and recipient target cells, transformation of immature embryo cells and subsequent regeneration of fertile transgenic plants are disclosed in U.S. Pat. Nos. 6,194,636 and 6,232,526, which are incorporated herein by reference.

The development or regeneration of plants including the foreign, exogenous isolated nucleic acid fragment that encodes a protein of interest is well known in the art. The regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention including the nucleic acid molecule encoding the $m^6A$ demethylase is cultivated using methods well known to one skilled in the art.

The seeds of transgenic plants can be harvested from fertile transgenic plants and be used to grow progeny generations of transformed plants of this invention including hybrid plants line for selection of plants having an enhanced trait. In addition to direct transformation of a plant with the nucleic acid molecule encoding the $m^6A$ demethylase, transgenic plants can be prepared by crossing a first plant having the nucleic acid molecule encoding the $m^6A$ demethylase with a second plant lacking the nucleic acid molecule. For example, the nucleic acid molecule encoding the $m^6A$ demethylase can be introduced into the first plant line that is amenable to transformation to produce a transgenic plant which can be crossed with a second plant line to introgress the nucleic acid molecule encoding the $m^6A$ demethylase into the second plant line. The transgenic plant derived from the plant cell of the present invention is cultivated to produce increased yield and/or biomass compared with a control plant. As used herein a "control plant" means a plant that does not contain the nucleic acid molecule encoding the $m^6A$ demethylase. A control plant is to identify and select a transgenic plant that has increased yield and/or biomass. A suitable control plant can be a non-transgenic plant of the parental line used to generate a transgenic plant, i.e. devoid of the nucleic acid molecule encoding the $m^6A$ demethylase. A suitable control plant may in some cases be a progeny of a hemizygous transgenic plant line that does not contain the nucleic acid molecule encoding the $m^6A$ demethylase, known as a negative segregant.

The "yield" of the transgenic plant described herein means the harvest amount of the product desired by the cultivation. The standards for evaluating the yields of different plants are different. For example, the subject of the evaluation of the yields of cereal crops (rice, wheat, maize, etc.), beans and oil crops (soybean, peanut, rape, etc.) is the seed (grain); that of cotton is the seed cotton or the lint cotton; that of yam crops (sweet potato, potato, cassava, etc.) is the tuberous root or tuber; that of bast fiber crops is the fiber of stems or the fiber of leaves; that of sugarcane is the stem; that of beet is the root; that of tobacco is the leaf; that of green manure crops (alfalfa, trefoil, etc.) is the stem and leaf, etc. The meaning of the yield of the same plant differs when it is cultivated for different purposes. For example, when maize is cultivated as food and fine feed crop, the yield is the harvest amount of grains, and when it is cultivated as silage, the yield includes the total harvest amount of stems, leaves and ears. The increased yield of the transgenic plant of the present invention may be measured by many means, including measuring weight, seed number per plant, seed weight, tuber weight, seed number per unit area (i.e. seeds, or weight of seeds, per acre), bushels per acre, tons per acre, kilo per hectare.

Those skilled in the art can determine the meaning of the yield for each plant and the standard for evaluating it according to the knowledge in the art.

Biomass means the total mass of the existing organic materials of an organism. It is expressed as dry weight, fresh weight, tiller number, etc. in the present invention. The increased biomass of the transgenic plant of the present invention may be measured by many means, including measuring weight, dry weight or fresh weight of the overground parts per plant, tiller number, dry weight of the overground parts per unit area (i.e. dry weight or fresh weight, per acre), bushels per acre, tons per acre, kilo per hectare.

EXAMPLES

The present invention is further illustrated in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Furthermore, various modifications of the invention in addition to those shown and described herein will be apparent to those skilled in the art from the foregoing description. Such modifications are also intended to fall within the scope of the appended claims.

Transformation Method of Tobacco

1. Materials:

Tobacco variety Burley 21; *Agrobacterium*: LBA4404; Ostreococcus RCC809 demethylase gene in pMG1 driven by a 35S promoter.

2. Tobacco Transformation

*Agrobacterium* cultures were grown from a single colony for 2-3 days at 28° C. in YEP (Yeast Extract Peptone Dextrose) medium containing 50 mg/L kanamycin, 25 mg/L rifamycin and 25 mg/L streptomycin. Explant material was obtained by growing sterilized seeds in magenta boxes for 3-5 weeks. Co-cultivation of sterile tobacco leaf material cut in 2 mm segments with the *agrobacterium* culture that has been diluted to 10-6 colony forming units for three days. Wash explants in MS+1 mg/L BA+0.1 mg/L NAA+250 mg/L carbenicillin liquid medium for 5 to 15 min Selection was performed on solid plants containing 50 mg/L kanamycin, 25 mg/L rifamycin and 25 mg/L streptomycin in YEP medium. Transgenic plants were regenerated in MS+1 mg/L IBA+150 mg/L Kn solid medium.

3. Seedling Vigor Screening

Tobacco seeds were sown on growing media containing peat moss and perlite. The seeds and seedlings were watered as needed with 125 ppm Miracle-Gro® fertilizer and maintained at 21° C. under 18 hours of LED grow lights.

4. Enhanced Root Development

Four-week-old tobacco seedlings were grown in in 2.7 liter pots. The plants were watered as needed with 125 ppm Miracle-Gro® fertilizer and maintained at 21° C. under 18 hours of LED grow lights.

5. Enhanced Plant Development and Faster Flowering

Four-week-old tobacco seedlings were grown in 2.7-liter pots. The plants were watered as needed with 125 ppm Miracle-Gro® fertilizer and maintained at 21° C. under 18 hours of LED grow lights.

6. Enhanced Salt Tolerance

Tobacco seedlings were sterilized and grown on MS medium+200 mM NaCl.

7. Enhanced Osmotic Tolerance

Tobacco seedlings were sterilized and grown on MS medium+300 mM mannitol.

Completer Vector and T-DNA Sequences

SEQ ID NO: 3-Ostreococcus RCC809 FTO gene in pFAT1

3874 bp linear DNA between T DNA right and left borders

REFERENCE 1 (bases 1 to 3874)

FEATURES Location/Qualifiers misc_feature 1 . . . 26
gene="Left Border T-DNA repeat"
misc_feature 27 . . . 92
gene="Cloning site"
misc_feature complement (93 . . . 336)
gene="CaMV 3' UTR"
gene complement (337 . . . 1131)
gene="npt11"
product="Kan resistance"
misc_feature complement (1132 . . . 1942)
gene="2× CaMV 35S promoter"
product="Strong promoter"
misc_feature 1943 . . . 2007
gene="Cloning site"
product="Multiple cloning site"
misc_feature 2008 . . . 2352
gene="CaMV 35S promoter"
misc_feature 2353 . . . 2358
gene="Cloning site"
CDS 2359 . . . 3609
gene="Ostreococcus RCC809 FTO"
product="RCC809 FTO gene"
misc_feature 3610 . . . 3848
gene="CaMV 3' UTR"
misc_feature 3849 . . . 3874
gene="Right Border T-DNA repeat"

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A transgenic plant, seed, or plant part comprising a polynucleotide expressing a recombinant polypeptide comprising an amino acid sequence of SEQ ID NO:1, the polynucleotide being operably linked to a plant expressible promoter, wherein the transgenic plant, seed, or plant part has enhanced salt stress tolerance compared to a control plant, seed, or plant part that does not express the recombinant polypeptide, wherein the transgenic plant, seed, or plant part is from a monocot or a dicot plant.

2. A method of increasing the yield of a plant comprising transforming said plant with a polynucleotide expressing a recombinant polypeptide comprising an amino acid sequence of SEQ ID NO:1, the polynucleotide being operably linked to a plant expressible promoter, wherein the plant has enhanced salt stress tolerance compared to a control plant that does not express the recombinant polypeptide, wherein the plant is a monocot or a dicot plant.

3. The transgenic plant, seed, or plant part of claim 1 that is, or is from, a dicot plant.

4. The transgenic plant, seed, or plant part of claim 3, wherein the dicot plant is selected from soybean, canola, tobacco, potato, alfalfa, cotton, sunflower, or cannabis.

5. The transgenic plant, seed, or plant part of claim 3, wherein the dicot plant is tobacco.

6. The transgenic plant, seed, or plant part of claim 1 that is, or is from, a monocot plant.

7. The transgenic plant, seed, or plant part of claim 6, wherein the monocot plant is selected from wheat, rice, corn, turfgrass or ornamental grass.

8. A transgenic plant, seed, or plant part comprising a polynucleotide that is at least 95% identical to a nucleic acid sequence of SEQ ID NO:2, the polynucleotide being operably linked to a plant expressible promoter, wherein the transgenic plant, seed, cell or plant part has enhanced salt stress tolerance compared to a control plant, seed, cell, or plant part that does not express the recombinant polypeptide, wherein the transgenic plant, seed, or plant part is from a monocot or a dicot plant.

9. The transgenic plant, seed, or plant part of claim 8 comprising a polynucleotide that comprises a nucleic acid of SEQ ID NO:2.

10. A method of increasing the yield of a plant comprising transforming said plant with a polynucleotide that is at least 95% identical to a nucleic acid sequence of SEQ ID NO:2, the polynucleotide being operably linked to a plant expressible promoter wherein the plant has enhanced salt stress tolerance compared to a control plant that does not express the recombinant polypeptide, wherein the plant is a monocot or a dicot plant.

11. The transgenic plant, seed, or plant part of claim 8 that is, or is from, a dicot plant.

12. The transgenic plant, seed, or plant part of claim 11, wherein the dicot plant is selected from soybean, canola, tobacco, potato, alfalfa, cotton, sunflower, or cannabis.

13. The transgenic plant, seed, or plant part of claim 11, wherein the dicot plant is tobacco.

14. The transgenic plant, seed, or plant part of claim 8 that is, or is from, a monocot plant.

15. The transgenic plant, seed, or plant part of claim 14, wherein the monocot plant is selected from wheat, rice, corn, turfgrass or ornamental grass.

16. The transgenic plant, seed, or plant part of claim 8 comprising a polynucleotide that is at least 99% identical to a nucleic acid sequence of SEQ ID NO:2.

* * * * *

SEQUENCE LISTING

```
Sequence total quantity: 3
SEQ ID NO: 1           moltype = AA  length = 416
FEATURE                Location/Qualifiers
source                 1..416
                       mol_type = protein
                       note = Ostreococcus sp. RCC809
                       organism = unidentified
SEQUENCE: 1
MLDDVLTPSD AGYDDVLRAH YDGFVVDDPG ALPASAHDDV RRAFQTMLEN GEFTHDVLQA  60
GQKVSRTFVR RVLLGERGCT YHYQRLRLFA QPWEGREAYD VVRELNERLK ERTRRALAAG  120
RHEKSECDYN VTLINYMETV EESEVALKDE TMYGLGATSV SWHSDSSLRE NSTVAVYHTY  180
AAPKRRDWCV ALRALNVECP VLRVPLEDRA TYYMCGDFNA THHHAVLTGS SARFSATHRV  240
GVVAKDTWKY IKKRCIDALR LVPELEGDRV LDAKKIQLLA EVHREVEFQW IRMFHLQGED  300
HARLHARYWK QRIDELTEAW DRMEMCFRKI LSKLKRSSSK TQPPRAYSMM LYAMTTVKEL  360
RDEHAKRCSA SAYAQLPPSC QPVDLPSYDD TSPLPFELKP VIVFIEEERD ARHGSK      416

SEQ ID NO: 2           moltype = DNA  length = 1251
FEATURE                Location/Qualifiers
source                 1..1251
                       mol_type = unassigned DNA
                       note = Ostreococcus sp. RCC809
                       organism = unidentified
SEQUENCE: 2
atgcttgacg atgtgctcac cccatcagat gctggttacg acgatgtctt gagggcccat  60
tatgatggct tcgttgttga tgatcctggt gctttgcctg cttcagcaca tgatgatgtt  120
aggagggctt ttcaaactat gcttgagaat ggcgagttta cacatgacgt actacaagct  180
gggcagaaag tttcaagaac attcgtgagg agggttcttc ttggcgaaag aggttgtact  240
taccactacc aaaggctaag gctttttgca cagccatggg agggaagaga agcctatgat  300
gttgttcgtg aattgaatga acgactgaag gaaagaaccc gtagagcctt agctgctggt  360
agacatgaaa aatctgaatg tgactataac gtcacattga taaattatat ggaaaccgta  420
gaggaatctg aggtcgcatt gaaggatgag actatgtacg gactaggtgc aacatcagtt  480
tcatggcaca gtgattcctc attgagggag aacagtacag ttgctgtgta tcacacatat  540
gctgcaccca aacgtagaga ctggtgtgtt gcacttagag cacttaacgt tgaatgtccc  600
gttctaagag tccctctcga agatagagca acatactata tgtgcggaga ttttaatgca  660
acacatcatc atgcagtgtt gactggttcc tcagcaagat tcagtgctac acatagggta  720
ggagttgtcg ctaaggatac ttggaagtat ataaaaaaga ggtgtattga cgctcttcgt  780
```

-continued

```
ctagttcctg agttagaggg agacagggtg ctggatgcta agaagatcca attgcttgct  840
gaggtgcata gagaggttga attccaatgg atcaggatgt ttcatcttca gggagaagat  900
cacgcacgac tccacgctag gtattggaag cagagaattg atgaactaac tgaggcatgg  960
gacagaatgg aaatgtgctt tcgaaagatc ctgagcaagc taaagaggtc atcatcaaag  1020
actcagccac caagggcata cagtatgatg ctctacgcca tgaccactgt taaagaactt  1080
cgagatgaac atgcaaaacg ttgcagcgct agcgcatatg ctcaattgcc acctagctgt  1140
caacctgtcg atctacccag ttacgatgac acttctcctc tcccatttga gcttaagccc  1200
gtgattgttt ttatcgagga agagcgtgat gcacgacatg ggtctaaatg a           1251

SEQ ID NO: 3           moltype = DNA  length = 3874
FEATURE                Location/Qualifiers
source                 1..3874
                       mol_type = unassigned DNA
                       note = Ostreococcus sp. RCC809
                       organism = unidentified
SEQUENCE: 3
tggcaggata tattgtggtg taaacaaatt gacgcttaga caacttaata acacattgcg  60
gacgttttta atgtactgaa ttaacgccga attaattcgg gggatctgga ttttagtact  120
ggattttggt tttaggaatt agaaatttta ttgatagaag tattttacaa atacaaatac  180
atactaaggg tttcttatat gctcaacaca tgagcgaaac cctataggaa ccctaattcc  240
cttatctggg aactactcac acattattat ggagaaactc gagcttgtcg atcgactcta  300
gctagaggat cgatccgaac cccagagtcc cgctcagaag aactcgtcaa gaaggcgata  360
gaaggcgatg cgctgcgaat cgggagcggc gataccgtaa agcacgagga agcggtcagc  420
ccattcgccg ccaagctctt cagcaatatc acgggtagcc aacgctatgt cctgatagcg  480
gtccgccaca cccagccggc cacagtcgat gaatccagaa aagcggccat tttccaccat  540
gatattcggc aagcaggcat cgccatgtgt cacgacgaga tcctcgccgt cgggcatgcg  600
cgccttgagc ctggcgaaca gttcggctgg cgcgagcccc tgatgctctt cgtccagatc  660
atcctgatcg acaagaccgg cttccatccg agtacgtgct cgctcgatgc gatgtttcgc  720
ttggtggtcg aatgggcagg tagccggatc aagcgtatgc agccgccgca ttgcatcagc  780
catgatggat actttctcgg caggagcaag gtgagatgac aggagatcct gccccggcac  840
ttcgcccaat agcagccagt cccttcccgc ttcagtgaca acgtcgagca cagctgcgca  900
aggaacgccc gtcgtggcca gccacgatag ccgcgctgcc tcgtcctgga gttcattcag  960
ggcaccggac aggtcggtct tgacaaaaag aaccgggcgc ccctgcgctg acagccggaa  1020
cacggcggca tcagagcagc cgattgtctg ttgtgcccag tcatagccga atagcctctc  1080
cacccaagcg gccggagaac ctgcgtgcaa tccatcttgt tcaatcccca tggtcgatcg  1140
acagatctgc gaaagctcga gagagataga tttgtagaga gagactggtg atttcagcgt  1200
gtcctctcca aatgaaatga acttccttat atagaggaag gtcttgcgaa ggatagtggg  1260
attgtgcgtc atcccttacg tcagtggaga tatcacatca atccacttgc tttgaagacg  1320
tggttggaac gtcttctttt tccacgatgc tcctcgtggg tgggggtcca tctttgggac  1380
cactgtcggc agaggcatct tgaacgatag cctttccttt atcgcaatga tggcatttgt  1440
aggtgccacc ttccttttct actgtccttt tgatgaagtg acagatagct gggcaatgga  1500
atccgaggag gtttcccgat attacccttt gttgaaaagt ctcaatagcc ctttggtctt  1560
ctgagactgt atctttgata ttcttggagt agacgagagt gtcgtgctcc accatgttat  1620
cacatcaatc cacttgcttt gaagacgtgg ttggaacgtc ttcttttttcc acgatgctcc  1680
tcgtgggtgg gggtccatct ttgggaccac tgtcggcaga ggcatcttga acgatagcct  1740
ttcctttatc gcaatgatgg catttgtagg tgccaccttc cttttctact gtccttttga  1800
tgaagtgaca gatagctggg caatggaatc cgaggaggtt tcccgatatt accctttgtt  1860
gaaaagtctc aatagccctt tggtcttctg agactgtatc tttgatattc ttggagtaga  1920
cgagagtgtc gtgctccacc atgttggcaa gctttggtgc gatcgctcct cctgcaggga  1980
agggtaaacg cgtaatctag agaattcccg atcctatctg tcacttcatc aaaaggacag  2040
tagaaaagga aggtggcact acaaatgcca tcattgcgat aaaggaaagg ctatcgttca  2100
agatgcctct gccgacagtg gtcccaaaga tggaccccca cccacgagga gcatcgtgga  2160
aaaagaagac gttccaacca cgtcttcaaa gcaagtggat tgatgtgata tctccactga  2220
cgtaagggat gacgcacaat cccactatcc ttcgcaagac ccttcctcta tataaggaag  2280
ttcatttcat ttggagagga cacgctgaaa tcaccagtct ctctctacaa gatctctaga  2340
cgatcgtttc gcggatccat gcttgacgat gtgctcaccc catcagatgc tggttacgac  2400
gatgtcttga gggcccatta tgatggcttc gttgttgatg atcctggtgc tttgcctgct  2460
tcagcacatg atgatgttag gagggctttt caaactatgc ttgagaatgg cgagtttaca  2520
catgacgtac tacaagctgg gcagaaagtt tcaagaacat tcgtgaggag ggttcttctt  2580
ggcgaaagag gttgtactta ccactaccaa aggctaaggc tttttgcaca gccatgggag  2640
ggaagagaag cctatgatgt tgttcgtgaa ttgaatgaac gactgaagga aagaacccgt  2700
agagccttag ctgctggtag acatgaaaaa tctgaatgtg actataacgt cacattgata  2760
aattatatgg aaaccgtaga ggaatctgag gtcgcattga aggatgagac tatgtacgga  2820
ctaggtgcaa catcagtttc atggcacagt gattcctcat tgagggagaa cagtacagtt  2880
gctgtgtatc acacatatgc tgcacccaaa cgtagagact ggtgtgttgc acttagagca  2940
cttaacgttg aatgtcccgt tctaagagtc cctctcgaag atagagcaac atactatatg  3000
tgcggagatt ttaatgcaac acatcatcat gcagtgttga ctggttcctc agcaagattc  3060
agtgctacac atagggtagg agttgtcgct aaggatactt ggaagtatat aaaaaagagg  3120
tgtattgacg ctcttcgtct agttcctgag ttagagggag acagggtgct ggatgctaag  3180
aagatccaat tgcttgctga ggtgcataga gaggttgaat tccaatggat caggatgttt  3240
catcttcagg gagaagatca cgcacgactc cacgctaggt attggaagca gagaattgat  3300
gaactaactg aggcatggga cagaatggaa atgtgctttc gaaagatcct gagcaagcta  3360
aagaggtcat catcaaagac tcagccacca agggcataca gtatgatgct ctacgccatg  3420
accactgtta aagaacttcg agatgaacat gcaaaacgtt gcagcgctag cgcatatgct  3480
caattgccac ctagctgtca acctgtcgat ctacccagtt acgatgacac ttctcctctc  3540
ccatttgagc ttaagcccgt gattgttttt atcgaggaag agcgtgatgc acgacatggg  3600
tctaaatgag agctctttct ccataataat gtgtgagtag ttcccagata agggaattag  3660
```

-continued

```
ggttcctata gggtttcgct catgtgttga gcatataaga aacccttagt atgtatttgt  3720
atttgtaaaa tacttctatc aataaaattt ctaattccta aaaccaaaat ccagtactaa  3780
aatccagatc ggtaagttgg cggccgcctt cgtttaaact atcagtgttt gacaggatat  3840
attggcgggt aaacctaaga gaaaagagcg ttta                              3874
```